United States Patent [19]

Wikswo, Jr. et al.

[11] 4,079,730

[45] Mar. 21, 1978

[54] APPARATUS FOR MEASURING EXTERNALLY OF THE HUMAN BODY MAGNETIC SUSCEPTIBILITY CHANGES

[75] Inventors: John P. Wikswo, Jr., Palo Alto; William M. Fairbank, Menlo Park; James E. Opfer, Palo Alto, all of Calif.

[73] Assignee: The Board of Trustees of the Leland Stanford Junior University, Stanford, Calif.

[21] Appl. No.: 697,724

[22] Filed: Jun. 21, 1976

Related U.S. Application Data

[62] Division of Ser. No. 511,456, Oct. 24, 1974, Pat. No. 3,980,076.

[51] Int. Cl.² ............................ A61B 5/02; A61B 5/05
[52] U.S. Cl. ............................ 128/2.05 F; 128/2.05 V; 324/201; 324/204; 324/224
[58] Field of Search ...................... 128/2.05 F, 2.05 V, 128/1.3–1.5; 324/43 G, 43 R, 34 FL, 34 S

[56] References Cited

U.S. PATENT DOCUMENTS

| | | | |
|---|---|---|---|
| 3,483,860 | 12/1969 | Namerow | 128/2.05 F |
| 3,789,834 | 2/1974 | Duroux | 128/1.3 X |
| 3,916,248 | 10/1975 | Nicol | 324/43 G |
| 3,965,411 | 6/1976 | Hesterman | 324/43 G X |

OTHER PUBLICATIONS

Wikswo, Jr.; J. P. et al., *A.I.P. Conf. Proc.*, (1973), No. 18, pp. 1335–1339.
Powner, E. T., et al., *Electronic Engng.*, Oct. 1970, vol. 42, No. 512, pp. 52–54.
Newbower; R. S., *IEEE Trans. on Magnetics*, vol. mag-9, No. 3, (Sep. 1973), pp. 447–450.

*Primary Examiner*—Kyle L. Howell

[57] ABSTRACT

An apparatus for measuring externally of the human body magnetic susceptibility changes within the body particularly the human heart and interpreting these changes in order to quantify the flow of blood.

6 Claims, 16 Drawing Figures

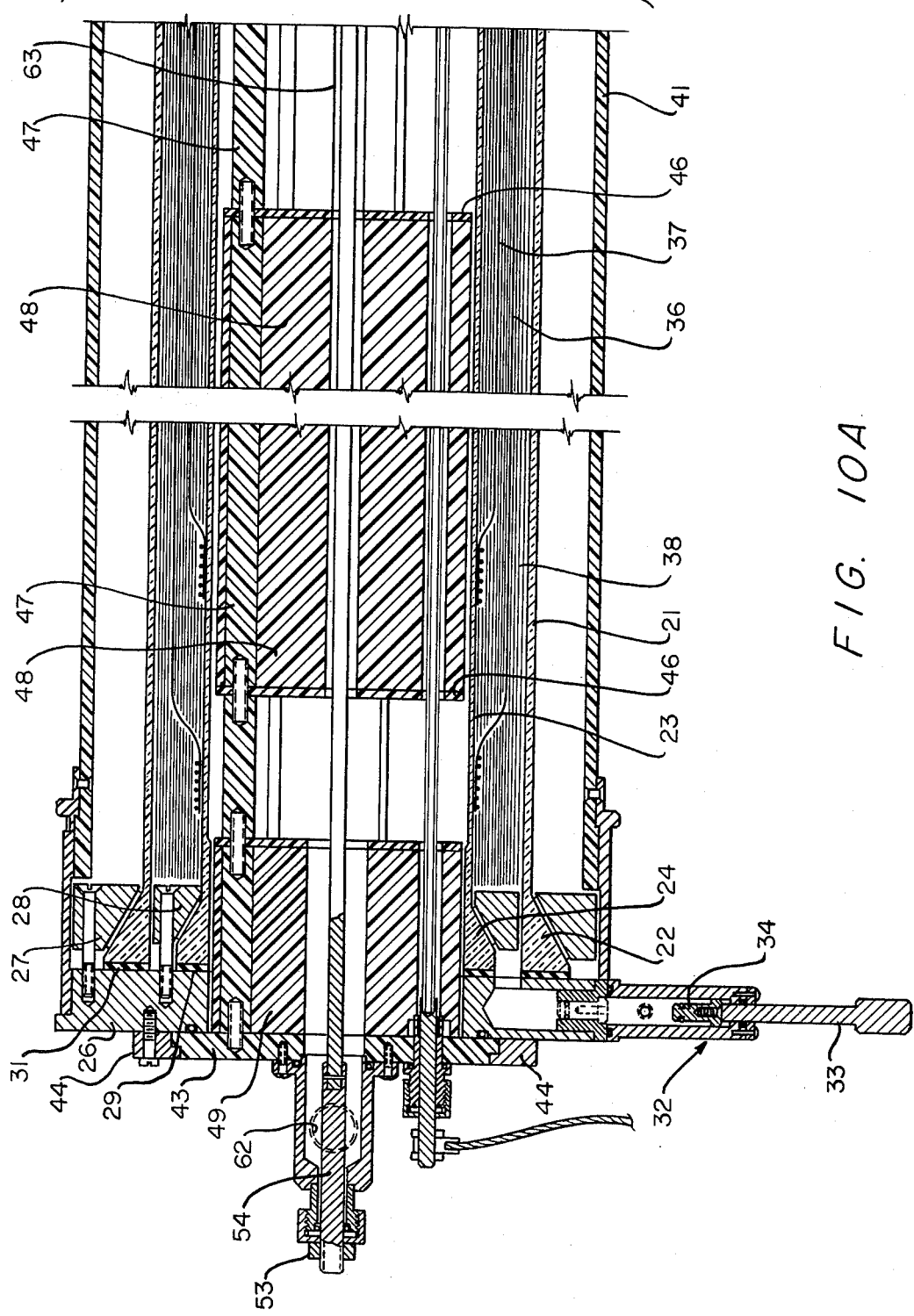

APPARATUS FOR MEASURING EXTERNALLY OF THE HUMAN BODY MAGNETIC SUSCEPTIBILITY CHANGES

GOVERNMENT CONTRACT

The Government has rights in this invention pursuant to Grant No. GI 34778 awarded by the National Science Foundation.

RELATED APPLICATION

This application is a division of application Ser. No. 511,456, filed Oct. 24, 1974, now U.S. Pat. No. 3,980,076.

BACKGROUND OF THE INVENTION

This invention relates generally to an apparatus for measuring blood flow by non-invasive measurement of magnetic susceptibility changes caused either by movement of blood or by variation in the magnetic susceptibility of the blood.

In the treatment of heart diseases it is important to determine the overall effectiveness of the heart as a pump, and to detect and quantify pathological conditions such as ventricular hypertrophy, stenotic or insufficient valves, and intra-cardiac shunts. The rate of cardiac volume change during contraction of the heart (systole) is related to the ventricular ejection velocity and can be used as a measure of myocardial contractility.

The prior art in cardiac output measurements can be divided into three general classes: invasive techniques requiring catheterization; invasive techniques not requiring catheterization; and non-invasive techniques.

In the invasive techniques requiring catheterization, a catheter is passed through an externally accessible vein or artery into the right or left chambers, respectively, of the human heart. Trans-septal venous catheterizations also provide access to the left chambers of the heart. In addition to being used to measure pressure and to withdraw blood samples from the heart, cardiac catheters may be used for measuring cardiac output.

One technique for measuring cardiac output relies upon the fact that the blood has a slight conductivity. As is known, when a conducting fluid moves in a direction perpendicular to the magnetic field an electromotive force is induced perpendicular to both the magnetic field and the direction of flow. This principle has been applied to catheter flowmeters including a self-contained catheter tip device and a catheter applied pair of sensing electrodes used in conjunction with an externally applied magnetic field. Induced voltages give an indication of the blood flow. The induced voltage depends upon the blood vessel diameter and the velocity and it is not possible to determine cardiac flow without knowledge of the vessel diameter.

Invasive techniques not requiring cathterization include fluorescence excitation in which a material is injected into the blood stream and the concentration of the material in the blood is periodically determined at different locations. Super-paramagnetic fluid tracers have also been used wherein the patient is injected with a super-paramagnetic fluid and the concentration of the super-paramagnetic tracer is determined magnetically.

Among the non-invasive techniques are pulse echo ultra-sound, Doppler ultra-sound, pulse pressure measurements, ballistocardiography and impedance plethysmography. In the latter, changes in total electrical thoracic impedance are measured by placing driving and sensing electrodes in relation to the heart-lung-diaphragm system. The measurement depends particularly upon electrode position, the current distribution through the thorax, the frequency of the driving signal, the rheologic properties of blood, and the fluid content of the lungs. Conventional impedance plethysmography has not been widely used for clinical measurements of cardiac output because of the major uncertainties in determining the above factors.

Another method using the same type of equipment is to make impedance measurements with an induction plethysmograph. This instrument operates on the principle that the magnitude of the eddy currents induced in a sample is proportional to the conductivity of the sample. This technique is subject to major limitations and has not yet been successfully applied.

In this method of induction plethysmography a transmitter coil is energized by sinusoidal current which creates a time varying magnetic field in its vicinity. A second coil located a fixed distance from the exciting coil acts as a receiver and the EMF induced in it is measured. An out-of-phase EMF is induced by the conductivity or eddy currents. In addition, an in-phase EMF is also induced in the receiver coil directly from the transmitter coil. This direct coupled or transformer voltage must be reduced to as low a value as possible by minimizing the mutual inductance and capacitance between the transmitter and receiver coils. A phase-sensitive detector is utilized to ensure that only the out-of-phase conductivity signal is observed. The magnitude of the transformer component precludes observation of the in-phase susceptibility signal. Thoracic conductivity measurement using such an instrument might also be applied to cardiac output determinations. This technique has two serious limitations when compared to susceptibility measurements in accordance with the present invention. The magnitude of the susceptibility related signal is proportional to the volume of the heart, whereas the magnitude of the conductivity related signal is proportional to the five thirds power of the volume. This implies that for a given stroke volume a larger conductivity signal will be produced by a larger heart. Thus, it would be difficult to use the conductivity signal for absolute measurements of cardiac output. In addition, such a measurement would be affected by the anisotropy of the conductivity of cardiac muscles and the variations of blood conductivity with hemocrit.

OBJECTS AND SUMMARY OF THE INVENTION

It is an object of the present invention to provide an improved non-invasive apparatus for measuring blood flow.

It is another object of this invention to provide an apparatus for measuring changes in the magnetic susceptibility of certain regions of the human body caused either by movement of the blood or by variation of the susceptibility of the blood.

It is a further object of the present invention to provide an improved compact apparatus for measuring the changes in magnetic susceptibility within the human body and particularly in the heart region.

It is another object of the present invention to provide an apparatus for measuring cardiac activity with a higher degree of accuracy than is now possible using non-invasive methods.

The foregoing and other objects of the invention are achieved by an apparatus including a supercooled volume containing a magnet for generating a magnetic field which extends into a body portion placed outside said volume and means within said supercooled volume for measuring changes of said field due to changes in susceptibility of said body portion.

BRIEF DESCRIPTION OF THE DRAWING

FIGS. 10A and 10B show an MSF susceptometer.

DESCRIPTION OF PREFERRED EMBODIMENTS

Generally, the invention is directed to an apparatus for measuring externally of the human body magnetic susceptibility changes within the body particularly the human heart and interpreting these changes in order to quantify the flow of blood.

It is known that blood is approximately as diamagnetic as water, having a magnetic susceptibility of $-0.7 \times 10^{-6}$ EMU/cm$^3$. The magnetic susceptibility of the heart and blood within it is substantially different from that of the surrounding tissue. Because of these susceptibility differences, changes in the total volume of the blood within the heart will result in small proportional changes in the magnetic field outside the body in the presence of an externally applied magnetic field.

Figure 1:
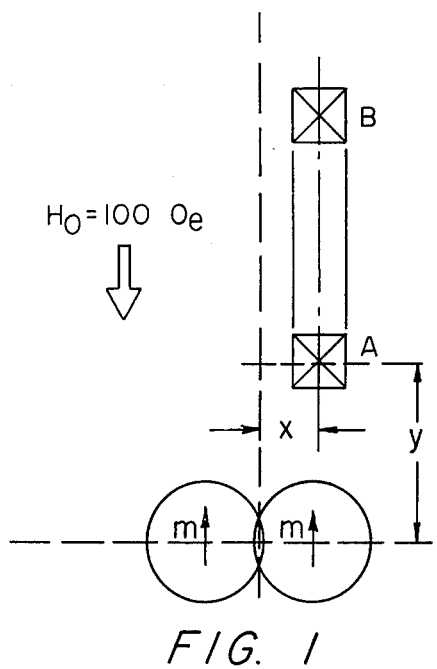
FIG. 1 shows a simple model of the heart associated with a magnetometer and magnetic field in two positions.

A simple model of the heart action demonstrates how the field changes can be detected. Consider an isolated sphere containing a given amount of blood, say 100 ml, as represented by the solid circle, FIG. 1. In a constant 100 gauss uniform field $H_O$, the induced d.c. magnetic moment, m, of this sphere is $0.7 \times 10^{-2}$ emu. A single Y axis magnetometer, A, is scanned past the sample at a fixed distance $y$. the magnetometer output plotted as a function of position will be similar to the solid curve in FIG. 2. If the sphere is then shifted 5 cm to the right, indicated by the dashed circle, and the scan is repeated, the output will resemble the dashed curve, FIG. 2. As the sample is moving back and forth in time both temporal and spatial field variations will be observed by a slowly scanning magnetometer. The transfer of blood from the ventricles to the arterial circulatory system during each contraction of the heart is represented by this simple model. In practice, observed field changes represent cardiac blood flow.

The main practical limitation in using a single magnetometer is that it is also sensitive to other external field changes. To minimize this problem, a second magnetometer, B, may be used so that the two magnetometers act as a gradient magnetometer or gradiometer, whose output is given by $$B_y^{GRAD} = B_y(A) - B_y(B) \quad (1)$$

Figure 2:
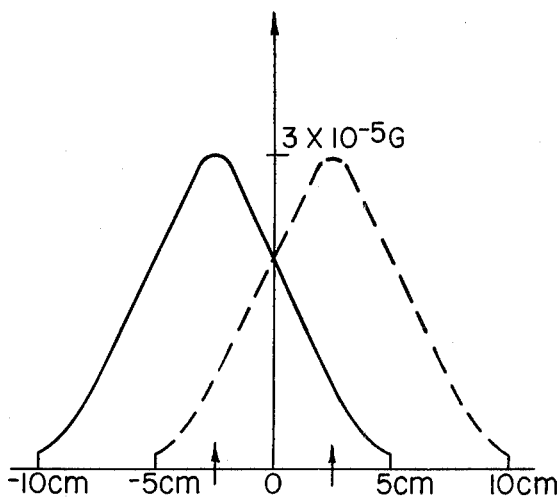
FIG. 2 shows the magnetometer output for the two positions.

Although such a gradiometer is not sensitive to uniform field changes, it will detect the moving sphere because the field change of A is an order of magnitude larger than that at B. The peak signal for the 100 ml sample in a 100 gauss field will be $3 \times 10^{-5}$ gauss when point A of the gradiometer is 7.5 cm from the sphere. The curves in FIG. 2 illustrate this response.

In a more realistic model of heart action, the overall effects of changes in the susceptibility of various regions of the body must be taken into account. In the presence of a constant applied field $\vec{H}_o(\vec{r})$ there exists in the body a small magnetization $\vec{M}(\vec{r},t)$ given by $$\vec{M}(\vec{r},t) = K(\vec{r},t)\, \vec{H}_o(\vec{r}) \quad (2)$$

where $K(\vec{r},t)$ is the volume susceptibility at point $\vec{r}$ at time $t$. External to the body the magnetic induction B from this magnetization is given by the superposition of dipole fields as $$\vec{B}(\vec{r},t) = \int \left[ \frac{3[\vec{M}(\vec{r}',t)\cdot(\vec{r}-\vec{r}')](\vec{r}-\vec{r}')}{|\vec{r}-\vec{r}'|^5} - \frac{\vec{M}(\vec{r}',t)}{|\vec{r}-\vec{r}'|^3} \right] d\vec{r}' \quad (3)$$

where integration is over coordinates of all points in the body. In terms of K and $H_o$ we have that $$\vec{B}(\vec{r},t) = \int K(\vec{r}') \left[ \frac{3[\vec{H}_o(\vec{r}')\cdot(\vec{r}-\vec{r}')](\vec{r}-\vec{r}')}{|\vec{r}-\vec{r}'|^5} - \frac{\vec{H}_o(\vec{r}')}{|\vec{r}-\vec{r}'|^3} \right] d\vec{r}' \quad (4)$$

A quantity such as the stroke volume of the heart can be estimated by interpreting $\vec{B}(\vec{r},t)$ in terms of simple models. If one characterizes the transfer of blood from the ventricles to the arterial circulation by the shift in position of a spherical volume V of blood, then the equation for B reduces to that of a moving magnetic dipole. The strength $m$ of this dipole is $KH_oV$ where $H_o$ is the applied field and K is the volume susceptibility of the blood. The induction at $\vec{r}$ when the dipole is located at $\vec{r}'$ is $$\vec{B}(\vec{r}) = \frac{-\vec{m}}{|\vec{r}-\vec{r}'|^3} + \frac{3[\vec{m}\cdot(\vec{r}-\vec{r}')](\vec{r}-\vec{r}')}{|\vec{r}-\vec{r}'|^5} \quad (5)$$

It must be emphasized that the spatial distribution of the field outside the body at any single instant does not readily yield information about the flow in the heart. Once the time dependence of the fields is measured, the situation changes. If one restricts his attention to time varying fields, then the integration in equation 4 need extend only over regions where the susceptibility changes significantly with time. The field changes arising from the movement of the heart and blood during the cardiac cycle will have a characteristic time dependence which will provide a means for identifying their sources. These changes in field arising from movement of material having a magnetic susceptibility different from that of surrounding material are termed magnetic susceptibility flow (MSF) signals.

In order to interpret the MSF signals, it is necessary to clarify the relationship between the observed MSF signals and the changes in susceptibility that occur within the thorax. It is important to note that the susceptometer measures magnetic field changes with respect to an arbitrary baseline. For convenience, one chooses this baseline to correspond to the field observed at end-diastole. The susceptibility at a point $\vec{r}$ at time $t$ may be written as $$K(\vec{r},t) = K(\vec{r},t_d) + \Delta K(\vec{r},t) \quad (6)$$

where $K(\vec{r},t_d)$ is the time independent end-diastolic susceptibility, $\Delta K(\vec{r},t)$ is the time-dependent susceptibility, and $t_d$ is the time of end-diastole. Thus, $$\Delta K(\vec{r},t) = K(\vec{r},t) - K(\vec{r},t_d) \quad (7)$$

Note that $$\Delta K(\vec{r},t_d) = 0 \quad (8)$$

For a constant magnetizing field $\vec{H}_o(\vec{r})$, the magnetization is given by $$\vec{M}(\vec{r},t) = \vec{H}_o(\vec{r}) K(\vec{r},t)$$

$$= \vec{H}_o(\vec{r}) [K(\vec{r},t_d) + \Delta K(\vec{r},t)]$$

$$= \vec{H}_o(\vec{r}) K(\vec{r},t_d) + \vec{H}_o(\vec{r}) \Delta K(\vec{r},t)$$

Thus, a constant magnetization $\vec{M}(\vec{r},t_d)$ and a time-dependent magnetization $\Delta \vec{M}(\vec{r},t)$ can be defined by $$\vec{M}(\vec{r},t_d) = \vec{H}_o(\vec{r}) K(\vec{r},t_d)$$

$$\Delta \vec{M}(\vec{r},t) = \vec{H}_o(\vec{r}) \Delta K(\vec{r},t)$$

so that $$\vec{M}(\vec{r},t) = \vec{M}(\vec{r},t_d) + \Delta \vec{M}(\vec{r},t) \quad (9)$$

This magnetization produces a magnetic induction at a point $\vec{r}$, and time $t$ given by $$\vec{B}(\vec{r},t) = \int \left\{ \frac{3\vec{M}(\vec{r}',t) \cdot (\vec{r}-\vec{r}')}{|\vec{r}-\vec{r}'|^5} (\vec{r}-\vec{r}') - \frac{\vec{M}(\vec{r}',t)}{|\vec{r}-\vec{r}'|^3} \right\} d\vec{r}'$$

Substituting for $\vec{M}(\vec{r},t)$ using Equation 9, it is possible to separate $\vec{B}(\vec{r},t)$ into constant and time dependent parts.

$$\vec{B}(\vec{r},t) = \vec{B}(\vec{r},t_d) + \Delta \vec{B}(\vec{r},t)$$

where $$\vec{B}(\vec{r},t_d) = \int \left\{ \frac{3\vec{M}(\vec{r}',t_d) \cdot (\vec{r}-\vec{r}')}{|\vec{r}-\vec{r}'|^5} (\vec{r}-\vec{r}') - \frac{\vec{M}(\vec{r}',t_d)}{|\vec{r}-\vec{r}'|^3} \right\} d\vec{r}'$$

and $$\Delta \vec{B}(\vec{r},t) = \int \left\{ \frac{3\Delta \vec{M}(\vec{r}',t) \cdot (\vec{r}-\vec{r}')}{|\vec{r}-\vec{r}'|^5} (\vec{r}-\vec{r}') - \frac{\Delta \vec{M}(\vec{r}',t)}{|\vec{r}-\vec{r}'|^3} \right\} d\vec{r}'$$

The temporal dependence of $\Delta \vec{B}(\vec{r},t)$ for a fixed $\vec{r}$ is the MSF signal as observed with the susceptometer of the present invention. In terms of the susceptibility distribution, $$\Delta \vec{B}(\vec{r},t) = \quad (10)$$

$$\int \Delta K(\vec{r}',t) \left\{ \frac{3\vec{H}_o(\vec{r}') \cdot (\vec{r}-\vec{r}')}{|\vec{r}-\vec{r}'|^5} (\vec{r}-\vec{r}') - \frac{\vec{H}_o(\vec{r}')}{|\vec{r}-\vec{r}'|^3} \right\} d\vec{r}'$$

Because $\Delta K(\vec{r},0)$ is uniformly zero, $\Delta \vec{B}(\vec{r},0)$ is uniformly zero.

Figure 3:
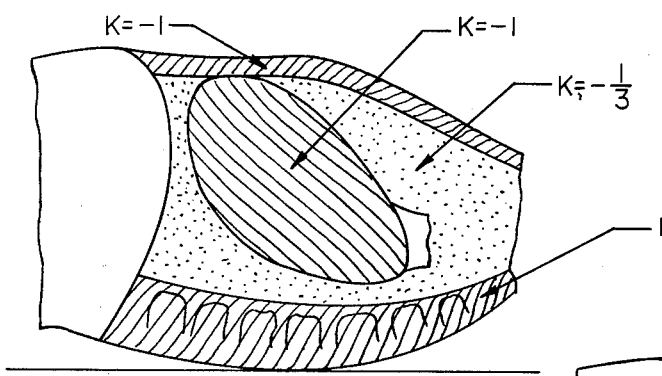
FIG. 3 shows the thoracic susceptibility distribution at diastole.
Figure 4:
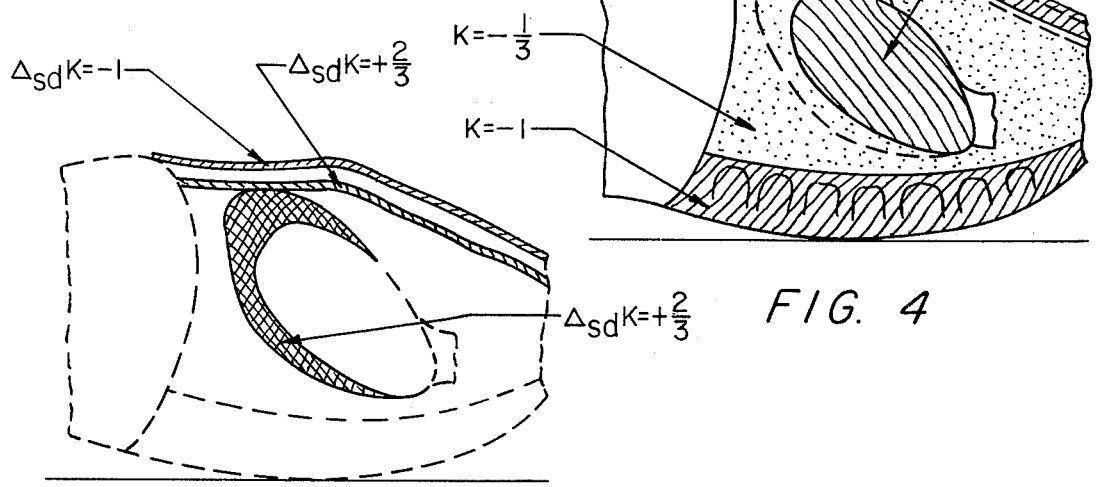
FIG. 4 shows the thoracic susceptibility distribution at systole.
Figure 5:
FIG. 5 shows the difference in susceptibility between diastole and systole.

FIG. 3 shows an approximate diastolic susceptibility distribution in a plane passing through the heart. To simplify the discussion, assume that blood, muscle and bone have a susceptibility of $-0.7 \times 10^{-6}$, lung tissue has a susceptibility of $-0.23 \times 10^{-6}$, and air has zero susceptibility. For convenience, we will normalize these susceptibilities to that of water, $-0.7 \times 10^{-6}$. Thus, the susceptibility of blood, muscle and bone will be taken as $-1$, that of lung tissue $-\frac{1}{3}$, and air will be non-magnetic with zero susceptibility. The systolic susceptibility distribution, with exaggerated anterior chest wall displacement, is shown in FIG. 4. The net susceptibility changes between systole and diastole are shown in FIG. 5. This model is limited by several assumptions: only three values of susceptibility, $-1$, $-\frac{1}{3}$ and 0, are used; the contribution of the blood entering and leaving the heart is ignored, and phasic volume changes within the heart are not considered. Even so, this model provides considerable insight about the MSF signal.

In order to determine cardiac output, it is necessary to determine the change in susceptibility distribution between end-diastole and end-systole. This change is given by Equation 7.

$$\Delta_{sd} K(\vec{r}) = K(\vec{r},t_s) - K(\vec{r},t_d) \quad (11)$$

where $t_s$ is the time of end-systole and $t_d$ is the time of enddiastole. This is shown in FIG. 5. $\Delta_{sd} K(\vec{r})$ is positive for some regions and negative for others, corresponding to a net decrease or increase in density of diamagnetic material at the point $\vec{r}$. Equation 10 is used to calculate $\Delta_{sd}\vec{B}(\vec{r})$, the field change occurring between end-diastole and end-systole $$\Delta_{sd}\vec{B}(\vec{r}) = \quad (13)$$

$$\int \Delta_{sd} K(\vec{r}') \left\{ \frac{3\vec{H}_o(\vec{r}')\cdot(\vec{r}-\vec{r}')}{|\vec{r}-\vec{r}'|^5}(\vec{r}-\vec{r}') - \frac{\vec{H}_o(\vec{r}')}{|\vec{r}-\vec{r}'|^3} \right\} d\vec{r}'$$

$\Delta_{sd}\vec{B}(\vec{r})$ can be measured directly because $\Delta\vec{B}(\vec{r},t)$ is the MSF signal observed with the susceptometer of the present invention.

Figure 6:
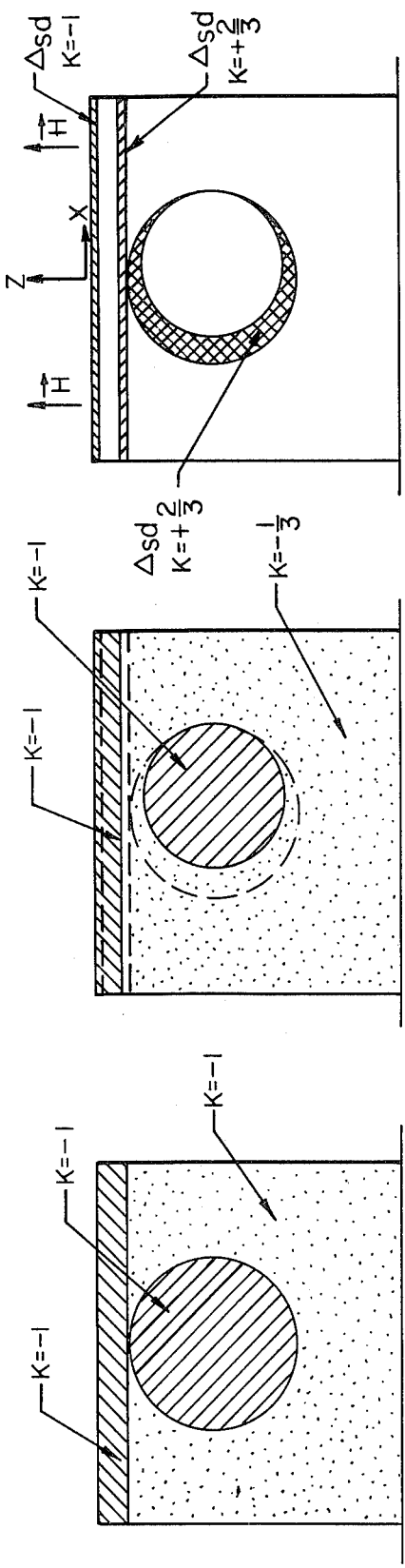
FIGS. 6A, 6B and 6C show a simple thoracic model corresponding to FIGS. 3, 4 and 5.

The contributions to $\Delta_{sd}\vec{B}(\vec{r})$ from cardiac volume change and chest wall motion must be estimated. FIGS. 6A–C show a simplified model which will be used for the calculations. The anterior chest wall is represented by a 2 cm. thick disc 25 cm. in diameter, with a susceptibility of $-0.7 \times 10^{-6}$. The lungs are uniform with a susceptibility of $-0.23 \times 10^{-6}$. The heart is assumed spherical, with a diastolic volume of 730 ml. and with its center 7 cm. from the anterior chest wall. The end-diastolic heart radius is 5.59 cm. At end-systole, the heart is also spherical, with a volume of 600 ml. and a radius of 5.26 cm. Thus, the change in radius between systole and diastole is 0.33 cm. If it is assumed that the position of the superior surface of the heart is fixed by the great viens, the center of the sphere will move 0.33 cm. towards the head during systole. The susceptibility distributions $K(\vec{r}, t_d)$, $K(\vec{r}, t_s)$ and $\Delta_{sd}K$ are shown in FIGS. 6A, 6B and 6C, respectively. Equation 13 and FIG. 6C can be used to calculate the MSF signal amplitudes arising from both heart and chest wall motion. The principle of superposition of fields allows us to write $$\Delta_{sd}\vec{B}(\vec{r})_{total} = \Delta_{sd}\vec{B}(\vec{r})_{heart} + \Delta_{sd}\vec{B}(\vec{r})_{chest\,wall}$$

To determine $\Delta_{sd}\vec{B}(\vec{r})_{heart}$, we must calculate the fields from the uniformly magnetized region defined by the two spheres. The magnetic fields outside of a uniformly magnetized sphere are identical to those of a single magnetic dipole moment at the center of the sphere, parallel to the sphere's magnetization and with a magnitude equal to the dipole density $\vec{M}(\vec{r})$ multiplied by the volume of the sphere. Two dipoles are chosen so as to obtain the desired source configuration. This process is shown schematically in FIG. 7. The large sphere has a volume of 730 ml. and a susceptibility of $\frac{2}{3}(0.7 \times 10^{-6}) = 0.47 \times 10^{-6}$. Thus, in a 100 oersted field, the magnetic moment associated with the large sphere is $$\vec{m}_1 = \vec{H} V_1 K_1 = 100 \times 730 \times 0.47 \times 10^{-6} \hat{e}_z\, EMU$$

$$\vec{m}_1 = 3.4 \times 10^{-2} \hat{e}_z\, EMU$$

The small sphere has a volume of 600 ml. and a susceptibility of $-\frac{2}{3}(0.7 \times 10^{-6}) = -.47 \times 10^{-6}$. In a 100 oe field, the magnetic moment associated with the small sphere is $$\vec{m}_2 = \vec{H} V_2 K_2 = 100 \times 600 \le (-0.47 \times 10^{-6})\hat{e}_z EMU$$

$$\vec{m}_2 = -2.8 \times 10^{-2} \hat{e}_z\, EMU$$

When a distributed dipole density $\vec{M}$ can be replaced by a set of discrete dipoles $\vec{m}_i$ located at points $\vec{r}_i$. Equation 13 reduces to (14)

$$\Delta_{sd}\vec{B}(\vec{r}) = \sum_i \frac{3\{\vec{m}_i \cdot (\vec{r}-\vec{r}_i)\}(\vec{r}-\vec{r}_i)}{|\vec{r}-\vec{r}_i|^5} - \frac{\vec{m}_i}{|\vec{r}-\vec{r}_i|^3}$$

Figure 7:
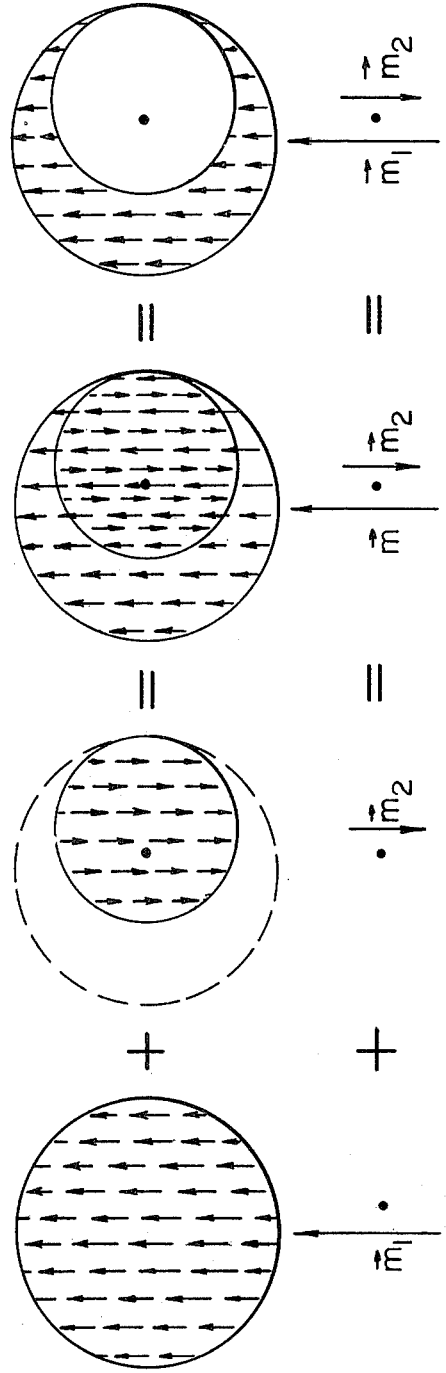
FIG. 7 shows the superposition of dipole fields.

One can use this equation to calculate the fields from the dipoles shown in FIG. 7, where $m_1 = 3.4 \times 10^{-2} \hat{e}_z\, EMU$ and $\vec{m}_2 = -2.8 \times 10^{-2} \hat{e}_z EMU$, with the dipoles located at $(-0.165, 0, -7)$ and $(0.165, 0, -7)$, respectively.

Figure 8:
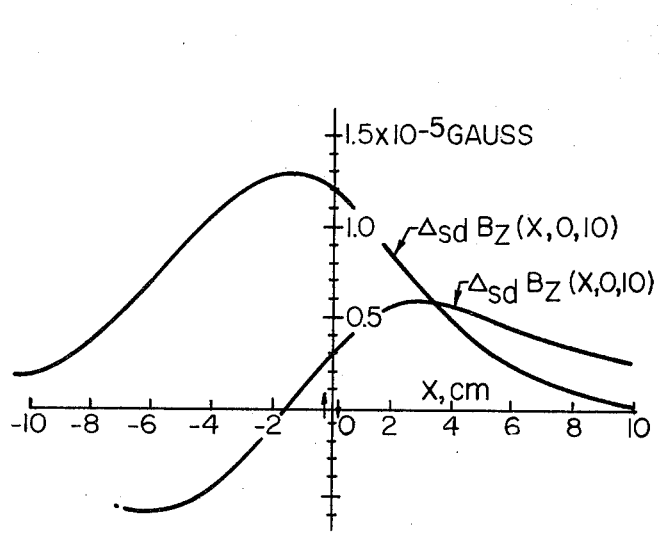
FIG. 8 shows the fields from a simple heart model.

The field components $\Delta_{sd}B_x(\vec{r})$ and $\Delta_{sd}B_z(\vec{r})$ are plotted in FIG. 8 as a function of $x$ for $y = 0$ and $z = 3$ cm. The peak in $\Delta_{sd}B_z$ is $1.3 \times 10^{-5}$ gauss and occurs for $x = 1.5$ cm. For comparison, a 130 ml. sphere representing the same volume change would have a moment of $$m_3 = 100 \times 130 \times 0.47 \times 10^{-6}\, 6.1 \times 10^{-3}\, EMU$$

For $z = 3$ cm. and $y = 0$, the peak in $\Delta_{sd}B_z$ would be $1.2 \times 10^{-5}$ gauss and occurs at $x = 0$. At $z = 0.5$ cm., the peak fields from the double and single dipole models are $3.2 \times 10^{-5}$ gauss and $2.9 \times 10^{-5}$ gauss, respectively.

To estimate $\Delta_{sd}B(\vec{r})_{chest\,wall}$, the contribution to the MSF by chest wall motion, one calculates the maximum fields from the two disks 25 cm. in diameter and $10^{-2}$ cm. thick, shown in FIG. 6C. The maximum field from a uniformly magnetized disk occurs on the axis and is given by $$\vec{B}(z) = B(z)\hat{e}_z = \frac{2KH\pi r^2 d}{[r^2 + (z-z')^2]^{3/2}} \hat{e}_z$$

where $B(z)$ is field magnitude at distance $(z-z')$ from disk;
$K$ is the susceptibility;
$H$ is the applied field;
$r$ is the disk radius;
$d$ is the disk thickness.

The maximum field change produced by the chest wall motion is thus $$\Delta_{sd}B_z(z) = \frac{2K_1 H\pi r^2 d}{[r^2 + (z-z_1)^2]^{3/2}} + \frac{2K_2 H\pi r^2 d}{[r^2 + (z-z_2)^2]^{3/2}}$$

where
$K_1 = 0.7 \times 10^{-6}$
$z_1 = 0$ cm.
$H = 100$ oe
$d = 10^{-2}$ cm.
$K_2 = \frac{2}{3} \times 0.7 \times 10^{-6}$
$z_2 = 2$ cm.
$r = 12.5$ cm.
$z = 3$ cm.
$= 0.47 \times 10^{-6}$ Substituting for the values, we find that at $z = 3$ cm.

$$\Delta_{sd}B_z = 3.23 \times 10^{-7}\,\text{gauss} - 1.89 \times 10^{-7}\,\text{gauss}$$

$$\Delta_{sd}B_z = 1.3 \times 10^{-7}\,\text{gauss}$$

Similarly, at $z = 0.5$ cm., the chest wall motion signal is $$\Delta_{sd}B_z = 1.4 \times 10^{-7}\,\text{gauss}$$

To summarize, the simple model predicts that the total MSF signal $\Delta_{sd}B_z$, measured at a point 3 cm. from the chest, will have a contribution of $1.3 \times 10^{-5}$ gauss caused by cardiac volume change and a contribution of $1.3 \times 10^{-7}$ gauss caused by motion of the anterior chest wall. Thus at 3 cm., there is only a 1% artifact. At 0.5 cm. from the chest wall, the fields are $3.2 \times 10^{-5}$ gauss and $1.4 \times 10^{-7}$ gauss, or 0.4%.

Figure 9:
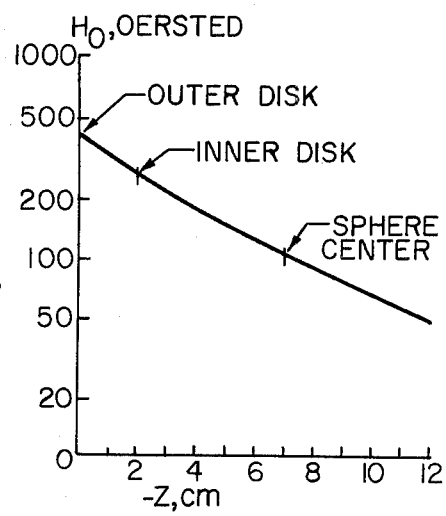
FIG. 9 shows the normalized axial magnetizing field.

One can estimate the correction to these numbers which results from the non-uniform magnetizing field. The axial magnetic field strength $H_z$ for the ring magnet is plotted as a function of $z$ in FIG. 9, normalized so that $H_z(0,0,-7) = 100$ oe. We will calculate the worst possible effect by assuming that $H_z$ is independent of $x$ and $y$, so that the field over a single disk is constant. Thus the upper disk is in a field of 450 oe, or 4.5 times greater than in the uniform field calculation. The lower disk is in a field of 260 oe, or 2.6 times greater than in the uniform field calculation. Thus, at $z = 3$ cm., the field from the two disks is $$\Delta_{sd}B_z = 4.5 \times 3.23 \times 10^{-7} \text{gauss} - 3 \times 1.89 \times 10^{-7} \text{gauss}$$

$$= 1.45 \times 10^{-6} \text{gauss} - 5.67 \times 10^{-7} \text{gauss}$$

or $$\Delta_{sd}B_z = 8.9 \times 10^{-7} \text{gauss}.$$

If we assume that the field throughout the sphere is equal to that at its center, the cardiac volume change will produce a signal of $1.3 \times 10^{-5}$ gauss. The maximum possible chest wall signal represents a 7% contribution. This calculation assumed that the entire chest wall was moving $10^{-2}$ cm., whereas only a small portion of chest moves with that amplitude. This also assumed that the magnetizing field for each disk was equal to the field at the center of the disk. In fact, the field at the edge is an order of magnitude smaller than that at the center. Also, the cardiac volume change signal is larger than $1.3 \times 10^{-5}$ gauss because of the non-uniform magnetization of the sphere. Thus, a 7% contribution represents a reasonable maximum value for the chest motion artifact.

Thus, a simplified model of heart and anterior chest wall motion has been described and equations developed that allow calculation of the field changes which are observed as the MSF signal. More complicated models would involve the integration of Equation 10 over the chambers of the heart. The contributions from cardiac motion and chest wall motion have been estimated and compared for both uniform and non-uniform magnetizing fields. With a uniform field, the contribution from chest wall motion is about 1% or less of the total signal. Several worst-case approximations were made in order to calculate the fields in the non-uniform case, and the contribution from the chest wall motion amounted to 7% of the total signal.

It is also possible to measure the magnitude and direction of the field at a plurality of points external to the body to gather sufficient information about $\Delta \vec{B}(\vec{r},t)$ for inversion of the field equations, giving an effective multipole moment at all times during the heart cycle. Because of the susceptibility difference mentioned before, this multipole moment will contain the information required not only to determine cardiac output and ejection velocity but also indicate the output of each heart chamber to detect the presence of intra-cardiac shunts, and valvular insufficiency.

Figure 10B:
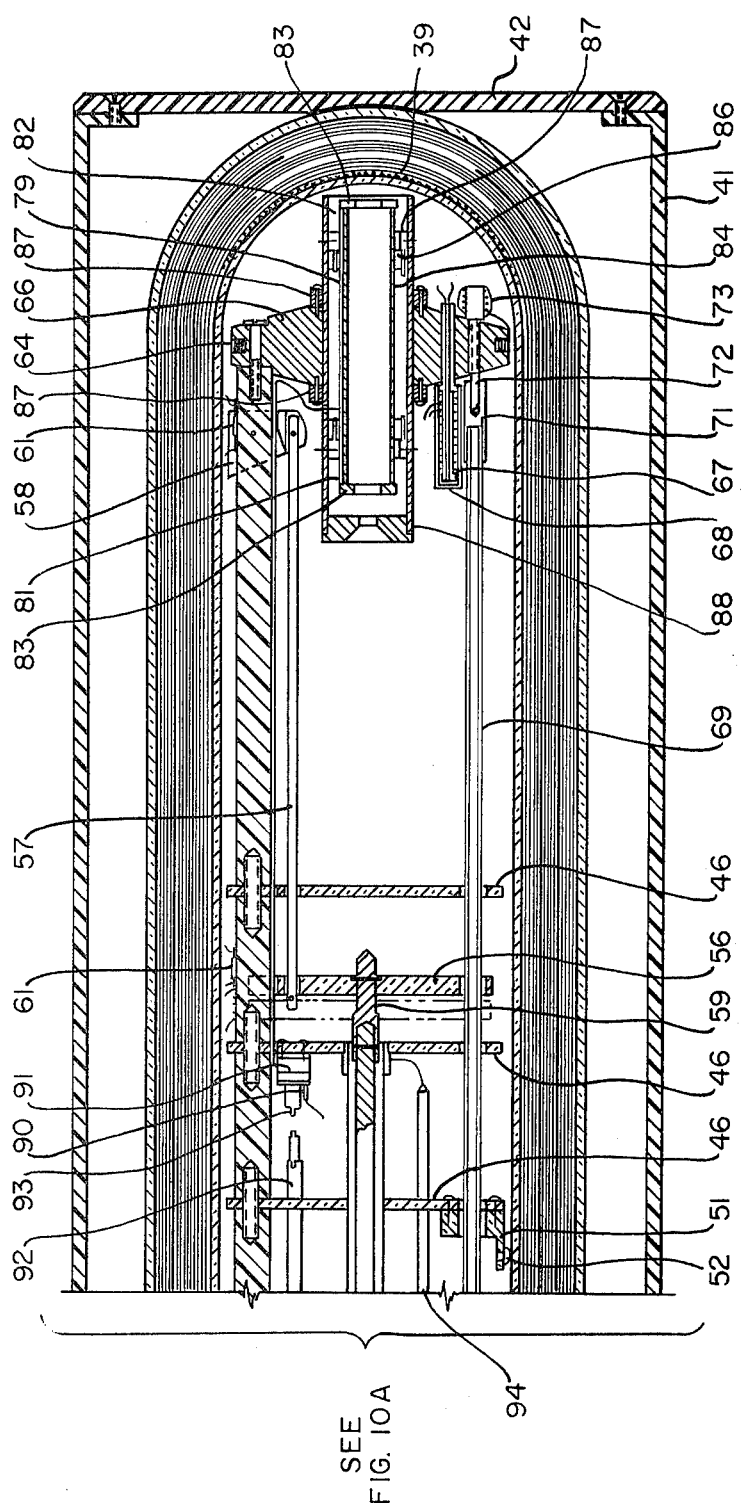

A susceptometer instrument capable of detecting the MSF signals is shown in FIG. 10. The instrument provides a constant magnetic field and detects the MSF signal while external magnetic noise is partially rejected.

Generally, the gradient magnetometer consists of a superconnecting flux transformer and a superconducting magnetometer. The flux transformer has two oppositely wound single turn coils which are connected to the magnetometer coupling coil by means of a low inductance shielded superconducting balanced line. The magnetometer is a mini-toroid SQUID with conventional RF and analog electronics. To ensure that the applied magnetizing field is constant, a persistent current superconducting magnet is used. Unwanted signals caused by the relative motion of the magnet and the flux transformer are minimized by making both part of the single rigid structure. The flux transformer is located symmetrically on the axis of a four inch diameter magnet capable of applying a 100 gauss field at a point 2 inches beyond the end of the Dewar which contains the magnetometer. The assembly is mounted in a super-insulated helium Dewar in such a manner that the lower coil of the flux transformer can be brought within one inch of an accessible external point. The design considerations that must be observed in the Dewar design are (1) rigidity of the Dewar system to avoid microphonics, (2) the use of gas cooled shields to avoid the necessity of a liquid nitrogen jacket which would contribute susceptibility noise, (3) the spacing of the Dewar walls such that the magnetometer coil can be placed close to the chest of the patient. It should be noted that various types of magnetometers could be used. The use of superconductors suggests Josephson magnetometers superconducting quantum intereference device (SQUID). However, with higher fields it would be possible to use a flux gate or similar type of magnetometer to detect that MSF signal.

A detailed drawing of a suitable susceptometer is shown in FIG. 10. The Dewar consists of a separate glass outer wall 21 with a standard glass tapered flange 22 at the top and a similar glass inner wall 23 with a top flange 24. The two Dewars' walls are clamped to an aluminum top plate 26 by clamp rings 27 and 28. Neoprene gaskets 29 and 31 provide the vacuum seal. The vacuum space is evacuated by means of a valve actuator 32 which attaches to the top plate 26. The handle 33 is used to remove sealing plug 34 while flushing and evacuating the vacuum space between the glass walls. The plug is seated in the top plate and the actuator is removed during normal operation of the susceptometer. Inside the vacuum space, there are two copper, wire-foil, gas-cooled radiation shields 36 and 37. A plurality of layers of perforated aluminized Mylar 38 act as radiation shields between the gas-cooled shields and the Dewar walls. Activated charcoal 39 is applied to the outer surface of the inner Dewar wall, as by epoxy, in order to provide cryogenic pumping of any helium gas that diffuses into the vacuum space. The Dewar is surrounded by a cylindrical cover 41 of fiberglass with a linen phenolic bottom 42.

The probe assembly is supported by a linen phenolic top plate 43 with a clamp ring 44. Spaced linen phenolic baffles 46 provide mechanical stability and also force the cold helium boiloff gas to cool the inner Dewar walls. The baffles are supported by spaced phenolic rods 47. The polyurethane foam plugs 48 and 49 also force the cold gas to flow near the Dewar wall for additional heat exchange. To prevent the probe from vibrating inside the Dewar, three spring clamps 51 with Nylon points 52 are attached to the third baffle.

A mechanically actuated clamp mechanism holds the lower end of the probe rigid with respect to the end of the Dewar. When the upper tension nut 53 is tightened, the central tension rod 54 raises the actuator disc 56. The disc then pulls three rods 57 to cause each of three cams 58 to rotate against the inner Dewar wall. The central tension rod engages the actuator disc by means of a bayonet pin 59 so that the rod can be removed for liquid helium transfers.

Five carbon resistors 61 are used to monitor the helium liquid level. During normal operation of the susceptometer, the helium boil-off gas is vented through the pump-out tube 62. The liquid nitrogen withdrawal tube, the liquid helium transfer tube, and the actuator rod are guided past the baffles by a Mylar tube 63.

The magnet assembly consists of a plurality of turns of copper stabilized, niobium titanium wire 64. In one instance 193 turns of 0.013 inch diameter wire were used. The wire is wound on a fiberglass-epoxy form 66. Adjacent turns are insulated by the copper oxide layer which covers the wire. Adjacent layers are separated by a layer of fiberglass cloth. Wire motion within the winding is avoided by coating the wire and fiberglass cloth with Dow Corning silicone vacuum grease which is rigid at cryogenic temperatures.

In order to operate the magnet in the persistent mode, a heat switched superconducting short is wired in parallel with the magnet. The heat switch consists of a bifilar winding of Manganin resistance wire wound on a Delrin form 67. The layer of Manganin wire is covered by a bifilar winding of niobium-titanium magnet wire. The Delrin form has a vent hole along its axis, and is covered by a gas-tight Delrin cover 68. When a current is passed through the Manganin wire, it heats the niobium-titanium wire above its superconducting transition temperature. Then the magnet winding and heat switch no longer forms a persistant loop and it is possible to charge the magnet by passing a current through the two removable charging leads, one of which is shown at 69. The lower end of the hollow copper leads are shunted with a length of niobium-titanium wire to minimize the heat dissipated into the helium during magnet charging. A spring loaded contact socket 71 is soldered to the end of each lead to provide a low resistance connection to the copper charging pins 72. The base of the charging pins supports the persistent joints between the magnet winding and the heat switch winding 73. To form such a persistent joint between two niobium-titanium wires, the oxide layer is removed over the end three feet of each wire by dipping the wire in a weak solution of hydrochloric acid. The copper is removed over a 12 inch length, starting 6 inches from the end, by dipping that portion of the wire in concentrated HCl. The two wires are held next to each other and the copper sections are soldered together with indium solder. This provides a stabilized, low resistance joint. The sections of the wire with no copper are then spot-welded together to form a persistent superconducting joint. The paired wire is then wrapped around the copper post, bound down firmly, and soldered again with indium solder to provide a low resistance path for charging the magnet.

Figure 11:
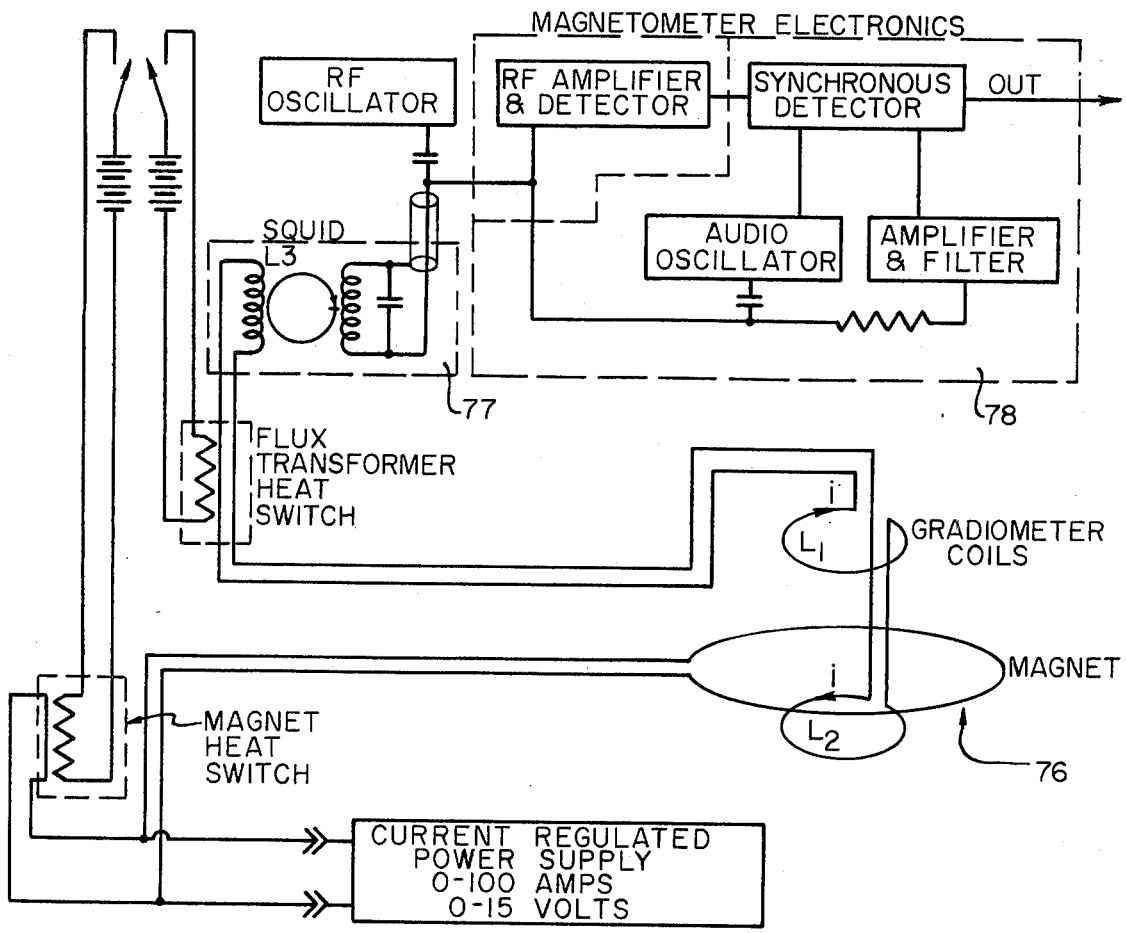
FIG. 11 is an electrical schematic diagram of the susceptometer of FIGS. 10A and 10B.

The gradient magnetometer is comprised to three subassemblies shown in FIG. 11: the superconducting flux transformer shown generally at 76; the SQUID 77; and the magnetometer electronics 78. The SQUID and the magnetometer electronics are commercially available. The gradiometer has three coils wound out of Formvar insulated niobium-titanium wire. The pick-up coils are wound on a quartz form which consists of several separate pieces of quartz glued together. The coupling coil is wound on Nylon fiber and is completely contained within the SQUID. As shown in FIG. 10, the wires between the coils are shielded by covering them with tin-lead tubing 79. In order to minimize gradiometer imbalance, the pick-up coils must be parallel and have the same diameter. The quartz form is designed with this in mind. The two pick-up coils 81 and 82 are wound in the corners where the end disks 83 are attached to the central tube 84. The central tube is supported by two quartz rings 86 which are held by retaining rings 87. The form is surrounded by a cylindrical fiberglass cover 88 which attaches the form to the magnet assembly. The two rings 87 can be adjusted to allow accurate centering of the coils with respect to the magnet. A coaxial carbon-resistor heat switch 90 can be used to release flux induced in the pick-up coils during magnet charging.

The toroidal SQUID 91 has a niobium point-contact as its critical element. A two-piece concentric screw-driver 92 is used to adjust the screw 93. The SQUID is coupled to the electronics by a copper coaxial cable 94.

Vacuum-tight electrical access for the heat switches, the level resistors, and the calibration coil is provided by two nine-pin hermetic connectors in the top plate. A simplified electrical schematic for the susceptometer is shown in FIG. 11.

Figure 12:
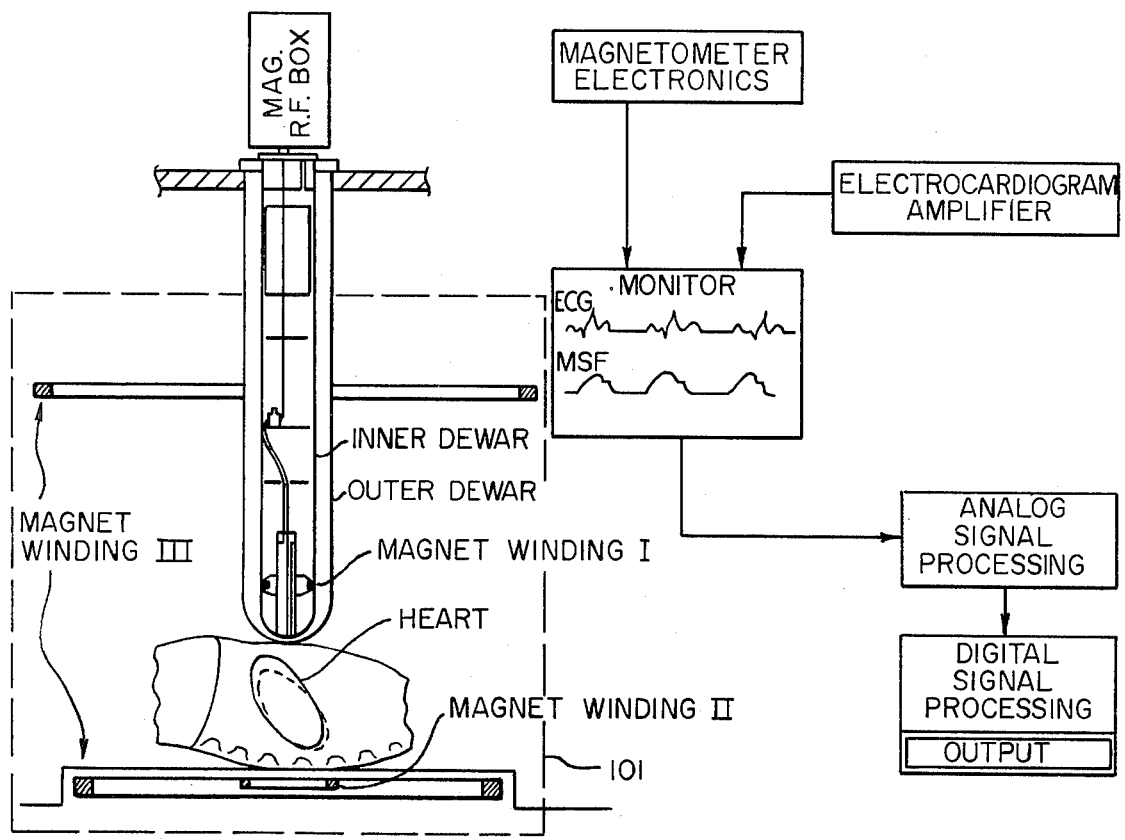
FIG. 12 shows a cardiac output measurement apparatus.

The complete system for measuring cardiac output is shown in FIG. 12. The magnetic shield 101 may be required in areas of high magnetic noise. Alternatively, the magnet and pick-up coils configuration can be adjusted to minimize the specific noise contributions. The magnetic field changes are converted to analog signals by the SQUID magnetometer and the superconducting magnetometer electronics. The susceptometer is supported over the patient's chest by a rigid mounting system and the position with respect to the patient's heart is encoded with potentiometers (not shown). Thus, it is possible to obtain the MSF signal at any desired position relative to the patient's heart.

Figure 13:
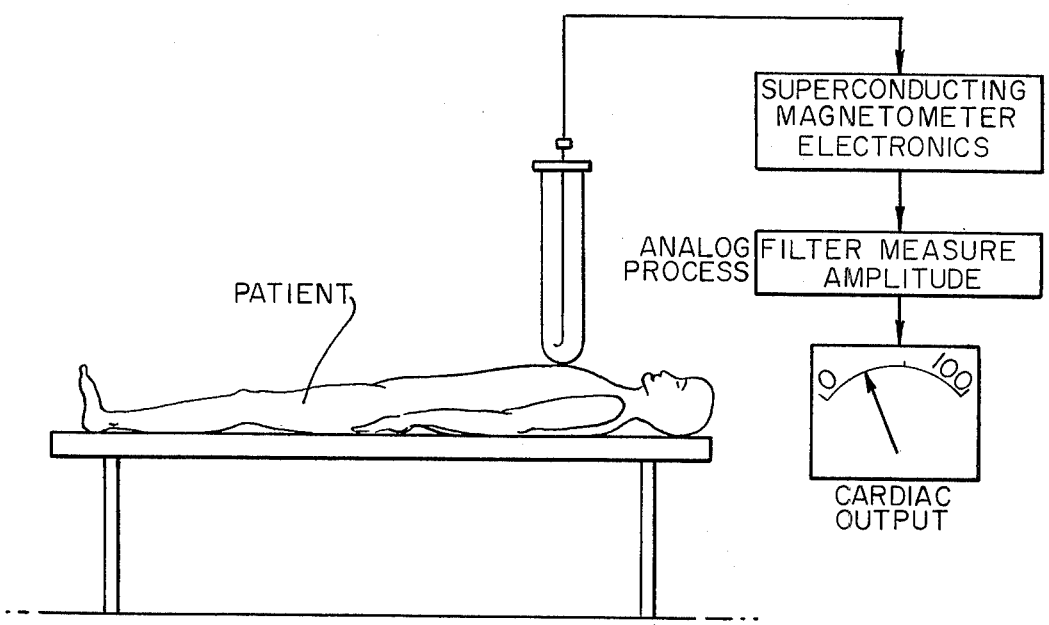
FIG. 13 schematically shows a cardiac output monitor.

If the instrument is placed in the position where the largest MSF signal is observed, then the amplitude of the MSF signal will be an indicator of cardiac output. The only electronic processing required would be analog filtering and measurement of the difference in signal amplitude between end-systole and end-diastole. This is shown schematically in FIG. 13. This type of instrument would be used, for example, in a coronary care unit to monitor a patient's cardiac output during a myocardial infarction or after cardiac surgery. The need for such an instrument is obvious. There are no other noninvasive instruments that can give a direct, real time indication of cardiac output without data reduction. The MSF cardiac monitor is simple enough to allow widespread application in coronary care units.

If the analog and digital processes shown in FIG. 12 are used, wide bandwidth (0.01–100 Hz) MSF signals can be obtained in a clinical environment. Obviously, the observed signals depend on the position and orientation of the heart relative to the instrument. Conventional X-ray and ultrasound techniques would be used to determine the position and orientation of the heart with respect to the xiphoid and the supersternal notch.

Using those two reference points, the computer controlled positioning system will allow the instrument to be placed at standarized locations relative to the heart itself, thereby minimizing any errors due to position uncertainty. If respiration appears to affect the signal, the patient can suspend respiration for the brief period required for each measurement.

There are several possible methods for reducing this data in order to obtain cardiac output information comparable to that obtained by cardiac catheterization. Included in these are pattern recognition, modeling, and field inversion.

Unlike imaging techniques such as X-ray and pulse-echo ultrasonic scanning, the MSF technique detects the magnetic fields of distributed dipole sources. Because the fields are characteristic of the sources, it is possible to gain considerable insight into the cardiac volume changes by studying only the field changes that is, by studying the MSF signals without reducing the data to obtain a detailed description of the heart. If a series of standardized MSF measurements is made on a large group of normal subjects and patients with clearly defined pathological conditions, it will be possible to create a set of normal and abnormal MSF templates based on sex, age and weight. The patient's MSF signals would be recorded and compared with the standard templates to determine the nature and severity of his cardiac disorder. This type of analysis could identify conditions such as high and low cardiac output and ventricular hypertrophy, in addition to measuring ejection velocity.

If quantitative volume change data is desired, it is necessary to obtain a more detailed description of the heart which, in turn, requires careful measurement of the external field distribution. The nature of the source would be determined either by actual inversion of the field equations or by modeling (equivalent to 3-dimensional curve fitting) in order to obtain an effective multipole moment for the source.

The simple moving sphere model described above indicates that a 5 cm. displacement of a 100 cm$^3$ sample will cause a 75% change in detected signal amplitude, whereas a 1 cm. displacement of the sample would cause a 10% change. When considering modeling or field inversion, the achievable resolution depends on how detailed a description of the external fields is achieved and how many higher order multipole moments are used to describe the source. The higher multipoles can be chosen so as to represent the individual chambers of the heart. Information about intracardiac shunts will follow immediately from the relative volume changes of the various compartments. It is realized that the heart is not an oscillating sphere of blood. However, such models are reasonable zeroth order representations of the pumping action of the heart. Obviously, there are a number of chambers emptying and expanding inside the heart during cardiac cycle and the magnetic susceptibility flow signal reflect this. The degree to which the contributions of the various chambers can be separated depends in part upon the knowledge of cardiac structure, the amount of data taken, and the extent of numerical data reduction.

Several possible sources of error have been suggested. These include (a) variation in the distance between the heart and the pick-up apparatus, both from subject to subject, and in a given subject during the beat as well as during the breathing cycle; (b) inclusion of the effect of variations in the blood content of the lungs; (c) variations in the shape and the orientation of the heart from subject to subject, as well as during the beat, and during the breathing cycle; (d) differences in the magnetic susceptibility of the blood from subject to subject; and (e) contamination by magnetic fields due to currents arising from EMF's that result from the rapid motion of blood through the strong magnetic field. Locating the instrument accurately with respect to the heart will be accomplished by means of the computer-controlled positioning system described above. Variations in the shape of the heart from subject to subject would automatically be taken into account with the equivalent source multipole calculation outlined above. Note that the blood flow information is contained in the calculated changes in the equivalent multipole. Thus, the variations between subjects (and their corresponding multipole equivalents) should not cause any difficulty.

The problem of the periodic redistribution of blood within the thorax is reduced to some extent by the $\frac{1}{3}$ dependence of the dipole field. The primary contribution to the signal will come from the heart, which is adjacent to the anterior chest wall; the contributions from other sources will be reduced because of their increased distance from the detector. The problem could also be solved by the effective multipole moment calculation.

The primary contribution to the magnetic susceptibility of living tissue is the diamagnetic susceptibility of water. The iron and oxygen which are present in oxygenated blood hemoglobin are molecularly bound in such a manner that there are no unpaired spins and no net magnetic moment. Because of this fact, arterial (fully oxygenated) blood is as diamagnetic as water, with $K = -0.72 \times 10^{-6}$. Venous blood will have a susceptibility of approximately $-0.69 \times 10^{-6}$, dependent to a slight extent on the degree of oxygenation of the blood. Variations in the level of oxygenation of the blood and blood hemocrit and the resulting susceptibility variations should cause less than a 1% error in the total cardiac output determination. The susceptibility of the lung tissue, which is the material displaced by the heart during the cardiac cycle, is also primarily due to the diamagnetism of water and has a value of $-0.23 \times 10^{-6}$.

Because blood is a good conductor, EMF's will be generated as the blood moves through the magnetic field. These EMF's will, in turn, produce eddy currents which will act as the source of magnetic fields. These fields will be at least three orders of magnitude smaller than the MSF fields and are thus unimportant.

It is apparent that other susceptometer designs can be used. Persistent mode superconducting magnets can be used to provide perfectly constant magnetic fields, or normal magnets with conventional regulated power supplies can be used. As shown in FIG. 12, the magnet can be an integral part of the susceptometer such as magnet winding I. The advantages of this configuration are mechanical rigidity, compactness, and localized sensitivity which may enhance resolution. The primary disadvantages are that the non-uniform magnetizing field complicates the problem of field inversion, and that the magnet and magnetometer cannot be separately scanned over the subject. It is also possible to use a magnet, normal or superconducting, placed beneath the subject as shown by magnet winding II in FIG. 12. The advantage of this configuration is that the sensitivity to volume changes in the posterior regions of the heart are enhanced because of their proximity to the magnet. The disadvantages are that the magnetizing field is non-uniform and it is difficult to obtain the necessary mechanical rigidity. One promising configuration is the use of a large Helmholtz magnet encompassing the magnet and the patient, such as magnet winding III. The advantages of this technique are the relative ease of inverting the field of equations with a uniform magnetizing field, and simplified mechanical stability requirements made possible by positioning the gradiometer in the central uniform field region of the magnet. The major limitation in field strength is the the power dissipation in the large resistive magnet winding.

The advantage of using a gradient magnetometer is that it provides a great degree of noise cancellation. Because of the large separation of the gradient coils shown in FIG. 12, the instrument acts as a true gradiometer only for distant sources. The fields from the heart coupled primarily to the lower coil, so that the magnitude, not the gradient, of the axis component of the MSF signal is observed. Using a different pick-up coil geometry, it would be possible to measure the $x$, $y$, and $z$ components. The gradient of the MSF signal could be measured by decreasing the distance between the gradient coils. Any of the nine field gradients could be measured. The gradient information would be useful in inverting the field equations.

If the applied field is strong enough, a fluxgate or other magnetometer could be used to detect the field changes caused by the cardiac volume changes. It may be useful to use the persistent superconducting flux transformer because it allows the magnetometer to operate in a low field and be sensitive to only changes in the field, not the field itself.

It is also possible to perform MSF measurements using the earth's magnetic field. However, the signals obtained are weak and special precautions should be taken to eliminate the contribution of other magnetic signals generated by the body.

In a clinical environment there is significant magnetic noise within the bandwidth 0-200 Hz. Because the bandwidth of the MSF signal is approximately 0.1-100 Hz, this presents some problems in the use of a constant field susceptometer. This can be overcome by using a alternating magnetic field susceptometer. If the magnetizing field alternates at a frequency $\nu_o$, then the measuring bandwidth can be restricted to frequencies $\nu$ such that $\nu_o - \nu_s \leq \nu \geq \nu_o + \nu_s$, where the signal occurs in the frequency range between zero and $\nu_s$. If $\nu_o$ is greater than the frequency of external magnetic noise, then the noise will not be in the signal bandwidth and cannot affect the measurement. The relative amplitude of the in-phase susceptibility signal and the out-of-phase conductivity signal is a strong function of frequency. For very low frequencies, the susceptibility signal dominates. The conductivity signal begins to dominate at frequencies for which the electromagnetic skin depth is less than a characteristic dimension of the object. Thus, to avoid distortion of the susceptibility signal, the magnetic field should alternate at a frequency $\nu_o$ so that $\nu_o - \nu_s$ is slightly greater than the highest noise frequency, thereby ensuring that no significant eddy currents are induced in the blood.

The present invention can be applied in the determination of peripheral blood flow. In the case of cardiac output, the magnetic susceptibility of the heart and the blood within it is substantially different from that of the surrounding tissue. Because of this susceptibility difference, changes in the total volume of blood within the heart will result in proportional changes in any externally applied magnetic field. In the case of peripheral blood flow, susceptibility changes will be due to both variation in the volume of blood in the vessels and variation of the magnetic susceptibility of the blood.

To facilitate understanding the measurement of peripheral blood flow, we must identify the mechanisms which will cause magnetic susceptibility changes in the regions of interest. In the arterial circulation, pulsatile flow will result in arterial volume changes during the cardiac cycle. Dependent upon the compressibility and density of the adjoining tissue, there will be proportional susceptibility changes which can be observed externally to that region by an external magnetic susceptometer. Thus, it would be possible to measure the volume changes within a limb due to pulsitile arterial flow and the changes in capillary and venous blood volume. These volume changes are directly related to blood flow and can thus be used as a measure of regional blood flow. It is also possible to magnetically label the blood. With existing techniques, injection of a labeling substance into the blood (i.e., dye, cold or warm saline, ascorbic acid) and sensitive detection of the appearance of this label downstream in the circulation allows determination of blood flow by the indicator dilution method. There are several possible means of magnetically labeling blood, both invasively and non-invasively. The appearance and washout of this magnetic label can be observed by the magnetic susceptometer described above. The most direct method for labeling is the injection of a strong paramagnetic substance, such as superparamagnetic iron colloids.

Calculations indicate that $10^{-4}$ grams of colloidal iron per 100 cc of blood would decrease the susceptibility of blood by a factor of two, and a milligram of colloid would change the sign of the susceptibility and increase its value by a factor of five. It would then be possible to use the susceptometer described above in order to observe the transit of this magnetically labelled bolus of blood through the region of interest.

It is also possible to change the magnetic susceptibility of blood non-invasively. The magnetic susceptibility of fully oxygenated blood is $-0.7 \times 10^{-6}$, approximately equal to that of water, and the magnetic susceptibility of completely deoxygenated blood is 20% lower. Thus, in normal circulation, arterial blood will have susceptibility of $-0.7 \times 10^{-6}$, whereas venous blood, which is approximately 80% oxygenated, will have a 4% smaller susceptibility. By changing the degree of oxygenation of either arterial or venous blood, it is possible to change its magnetic susceptibility. This change could be detected by an external magnetic susceptometer. In addition, the magnetic susceptibility of blood that has been exposed to carbon monoxide is identical to fully oxygenated blood. However, because carbon monoxide is not removed in the capillary circulation, blood that has been exposed to carbon monoxide will appear in the venous circulation with a susceptibility of $-0.7 \times 10^{-6}$. This means that it would be possible to quickly change the magnetic susceptibility of venous blood by having the patient inhale a single breath of carbon monoxide. There would be a sudden increase in the magnetic susceptibility of the venous blood, and the susceptometer could be used to observe the transit the bolus of labelled blood through the venous circulation. It may be possible to use both noninvasive labeling techniques in order to determine regional blood flow and regional oxygenation.

It seems likely that injected magnetic tracers could be of considerable clinical value and, in the low doses required with our sensitive magnetometers, of low toxicity. The ultimate usefulness of this technique as a clinical tool depends on the result of toxology studies preceding the use of the magnetic fluids in humans. The use of injected magnetic tracers promises, however, to be an important technique in animal studies. The MSF technique would permit determination of blood flow to the extremities, which would be useful in detection of occlusive peripheral vascular disease, and in the study of the effects of pharmacologic agents on peripheral circulation. If the susceptibility of the blood were altered, either invasively or non-invasively, it would be possible to determine regional blood flow and regional oxygenation to both the brain and certain visceral organs.

The present invention provides an improved apparatus which involves the direct non-invasive observation of the motion of blood in the heart with sufficient spatial resolution to be able to resolve the various chambers of the heart. The apparatus directly measures the stroke volume of the heart and gives information about the velocity of ejection from the ventricles, thus providing some measure of ventricular contractility. The apparatus allows a calibrated signal to be observed as a function of time so that cardiac output and ejection velocity can be continuously monitored in real time without the necessity of extensive calculations for the reduction of the signal. The apparatus is non-invasive and thereby is valuable for screening apparently healthy people for the presence of heart disease and also for following quantitatively the course of a patient's cardiovascular disease. There is provided an improved apparatus for non-invasively measuring blood flow.

We claim:

1. Apparatus for measuring changes in the magnetic susceptibility of selected portions of a living body placed adjacent thereto comprising means providing a supercooled volume, a magnet disposed in said supercooled volume to generate a magnetic field which extends outside of said volume into said selected portions of the adjacent living body, a magnetometer disposed in said supercooled volume and adapted to measure changes in the magnetic field in said volume indicating changes in susceptibility of said adjacent body portions, and means for processing said signals to indicate said changes.

2. Apparatus as in claim 1 wherein said means forming said supercooled volume comprises Dewar flasks.

3. Apparatus as in claim 1 wherein said magnetometer is a super conducting quantum interference device.

4. Apparatus as in claim 1 wherein said magnet is an electromagnet.

5. Apparatus as in claim 1 wherein said magnetometer is a gradient magnetometer positioned rigidly with respect to said magnet.

6. Apparatus as in claim 1 in which said magnetometer includes means for determining the magnitude and direction of the magnetic field.

* * * * *